United States Patent [19]
Hogt et al.

[11] Patent Number: 5,405,918
[45] Date of Patent: Apr. 11, 1995

[54] (POLY)SULFIDE CONTAINING POLYCITRACONIMIDES AND POLYITACONIMIDES

[75] Inventors: Andreas H. Hogt, Enschede; Auke G. Talma, Bathmen; Rudolf F. de Block, Deventer, all of Netherlands

[73] Assignee: Akzo Nobel N.V., Arnhem, Netherlands

[21] Appl. No.: 50,108

[22] PCT Filed: Oct. 29, 1991

[86] PCT No.: PCT/EP91/02049

§ 371 Date: Apr. 28, 1993

§ 102(e) Date: Apr. 28, 1993

[87] PCT Pub. No.: WO92/07828

PCT Pub. Date: May 14, 1992

[30] Foreign Application Priority Data

Oct. 29, 1990 [EP] European Pat. Off. ............ 90202864

[51] Int. Cl.$^6$ ................................................ C08F 8/32
[52] U.S. Cl. .................................... 525/375; 548/521; 548/545
[58] Field of Search ................. 525/375; 548/521, 545

[56] References Cited

U.S. PATENT DOCUMENTS

| | | | |
|---|---|---|---|
| 3,297,713 | 1/1967 | Ladd | 260/326.3 |
| 3,920,617 | 11/1975 | Hirosawa et al. | 260/77.5 |
| 3,974,163 | 8/1976 | Coran et al. | 260/281 GP |
| 4,254,229 | 3/1981 | Schwimdt et al. | 521/163 |

FOREIGN PATENT DOCUMENTS

| | | |
|---|---|---|
| 738500 | 12/1966 | Canada . |
| 0191931 | 8/1988 | European Pat. Off. . |
| 0345825 | 12/1989 | European Pat. Off. . |
| 1257913 | 4/1960 | France . |
| 61-014238 | 1/1986 | Japan . |

OTHER PUBLICATIONS

Krashnennikov et al, High–temperature vulcanisation of unsaturated rubbers by thio derivatives of maleimide. Int'l Polymer Science & Technology, vol. 2 No. 6 1975, pp. 68–71.

Prashchikina et al. Influence of the type and concentration of crosslinking agent on the effectiveness of a combined system of bismaleimide and sulphur. Int'l Polymer Science and Technology, vol. 17, No. 11, 1990, pp. T/1–T/4.

Baker et al. Advances in natural rubber for tires: compounding for improved wear, Elastomerics, Jul. 1989, pp. 20–25.

Praschikina et al. High–Temperature curing of general–purpose rubbers with a curing system comprising a bismaleimideamd sulpur Int'l Polymer Science and Technology vol. 4 No. 12, 1977, pp. T/48–T/50.

Dr. Grunewald, Physikalische und chemische Aspekte der Reversion Kautschuk & Gummi Kunststoffe 34, Jahrgang, No. 9/81, pp. 722–724.

The Synthesis of Bisitaconamic Acids and Isomeric Bisimide Monomers Journal of Polymer Science: Polymer Chemistry Edition, vol. 20, 233–239 (1982) pp. 233–239.

Galanti et al. The Synthesis of Biscitraconimides and Polybiscitraconimides. Journal of Polymer Science: Polymer Chemistry Edition, vol. 19 (1981) pp. 452–474.

(List continued on next page.)

*Primary Examiner*—Paul R. Michl
*Assistant Examiner*—Edward Cain
*Attorney, Agent, or Firm*—Ralph J. Mancini; Louis A. Morris

[57] ABSTRACT

Novel polysulfide-containing polycitraconimides and polyitaconimides are disclosed. Further, a process for the sulfur-vulcanization of rubber using these novel compounds is also disclosed. Also, a sulfur-vulcanized rubber product and articles of manufacture embodying this product are disclosed. Finally, the use of the novel polysulfide-containing polycitraconimides and polyitaconimides as anti-reversion coagents in the sulfur-vulcanization of rubber is also disclosed.

14 Claims, No Drawings

OTHER PUBLICATIONS

Hartford et al. Synthesis of N-Substituted bisitaconimide Monomers for Use as Thermosetting Polyimide Resins, Journal of Polymer Science: Polymer Chemistry Edition, vol. 16, 137–153 (1978).

Dr. K. H. Nordsiek, Rubber microstructure and reversion, Rubber World 197 (3), (1987) pp. 30–38.

P. O. Tawney et al. Vulcanization with maleimides. Journal of Applied Polymer Science vol. 8, 1964, pp. 2281–2298.

Chauchich, T. A. et al. Change in the structure and properties of vulcanizates based on natural, rubber under prolonged vulcanization in the presence of vulcanizing systems containing sulfur and bismaleimides. (USSR) Kauch, Rezina 1981, 95: 8561r.

Krasheninnikov et al. Vulcanization of cis –1,4–isoprene rubber by derivatives of maleimide under the action of high temperatures and radiation. International Polymer Science and Technology, vol. 1, No. 5, 1974. pp. T/57–T/59.

(POLY)SULFIDE CONTAINING POLYCITRACONIMIDES AND POLYITACONIMIDES

This invention relates to a new class of compounds, namely (poly)sulfide containing polycitraconimides and (poly)sulfide containing polyitaconimides. The invention also relates to a rubber composition having improved physical properties, which rubber composition is vulcanized with sulfur in the presence of one or more of the compounds of the present invention. The invention also relates to a sulfur-vulcanization process which is carried out in the presence of the particular compounds of the present invention and to the use of these compounds in the sulfur-vulcanization of rubber. Finally, the invention also relates to rubber products comprising rubber which has been vulcanized with sulfur in the presence of the compounds of the present invention.

Polycitraconimides and polyitaconimides are, in general, well known materials which may be prepared by the methods disclosed in, "The synthesis of Biscitraconimides and Polybiscitraconimides," Galanti, A.V. and Scola, D.A., Journ. of Polym. Sci.: Polymer Chemistry Edition, vol. 19, pp. 451–475, (1981); "The synthesis of Bisitaconamic Acids and Isomeric Bisimide Monomers," Galanti, A.V. et al., Journ. Polym. Sci.: Polymer Chemistry Edition, Vol. 20, pp. 233–239 (1982); and, Hartford, S.L., Subramanian, S. and Parker, J.A., Journ. Polym. Sci.: Polymer Chemistry Edition, Vol. 16, p. 137 (1982), the disclosures of which are hereby incorporated by reference.

In addition, some sulfur-containing imides are known from U.S. Pat. No. 3,974,163. In these imides, however, the sulfur is bonded directly to the imido nitrogen and thus, these materials behave in a significantly different manner than the imides of the present invention. Also disclosed in this patent is the use of these sulfur-containing imides as inhibitors of premature vulcanization of diene rubbers. However, the particular advantages of the compounds of the present invention are neither disclosed nor suggested by this publication. European patent application 345 825 also discloses sulfur-containing imides including N,N'-(thiodi-p-phenylene) bis-maleimide, N,N'-(dithiodi-p-phenylene) bismaleimide, and N,N'-(sulfodi-pphenylene) bismaleimide. Also disclosed in this publication is the use of these imides in the vulcanization of rubber compositions with sulfur. However, this patent publication does not teach or suggest the sulfur-containing citraconimides of the present invention and the compounds of this publication are inferior to the present citraconimdes as sulfur-vulcanization coagents.

In the tire and belt industries, among others, better mechanical and heat resistance properties are being demanded. It has long been known that the mechanical properties of rubber can be improved by using a large amount of sulfur as a cross-linking agent to increase the cross-link density in vulcanized rubbers. However, the use of large amounts of sulfur suffers from the disadvantage that it produces reversion and leads to a marked decrease in heat resistance and resistance to flex cracking, among other properties, in the final product. The fact that reversion is a continuing problem can be seen from, "Rubber Microstructure and Reversion," Nordsiek, Dr. K.H., Rubber World, 197 (3), pp. 30–38, 1987, and, "Physikalische und Chemische Aspekte der Reversion," Kautschuk+Gummi—Kunstoffe, 34, No. 9, 1981.

In order to eliminate the foregoing disadvantage, it has been proposed to add coagents to sulfur-vulcanization systems. One known type of coagent are the maleimides. Such vulcanization systems are disclosed in, "Vulcanization With Maleimides," Journal of Applied Polymer Science, Vol. 8, pp. 2281–2298 (1964).

U.S. Pat. No. 3,297,713 suggests the use of dithiobis (N-phenylmaleimides) as vulcanizing agents for rubber. However, this system does not employ sulfur as a vulcanization agent and thus suffers from several disadvantages which result from the absence of sulfur cross-links in the rubber product.

Japanese patent publication J6 1014-238 discloses sulfur-vulcanization systems wherein maleimides are used as coagents and which also contain either dibenzothiazyl disulfide or tetramethylthiuram disulfide. However, this solution is of limited application since only vulcanization accelerators having relatively short scorch times can be used with the bis-maleimides.

European patent application 0 191 931 suggests that the use of a bismaleimide compound in combination with a sulfenamide and a dithiophosphoric acid leads to further improvements in the mechanical and anti-reversion properties of sulfur-vulcanized rubbers. The patent specification claims that these rubbers exhibit improved resistance to reversion, resistance to heat ageing and resistance to flex cracking. However, this system is limited to vulcanization carried out in the presence of a sulfenamide accelerator in combination with a dithiophosphoric acid accelerator and is thus of limited utility in actual practice.

In the article, "Change in the Structure and Properties of Vulcanizates Based on Natural Rubber Under Prolonged Vulcanization in the Presence of Vulcanizing Systems Containing Sulfur and Bismaleimides," Chavchich, T.A., et al., Kauchuk i Rezina, vol. 4, pp. 20–3, 1981, there is disclosed that vulcanization of natural rubber tread stocks with sulfur in the presence of m-phenylenebis-maleimide at 143° C. over a 600-minute period gave vulcanizates with enhanced physiomechanical properties and resistance to reversion.

Other articles relating to the sulfur-vulcanization of rubbers using bismaleimides as coagents include, "Vulcanization of cis-1,4-isoprene rubber by derivatives of maleimide under the action of high temperatures and radiation," Kauchuk i Rezina, vol. 3, pp. 10–12, 1974; "High-temperature Vulcanization of Unsaturated Rubbers by Thio Derivatives of Maleimide," Kauchuk i Rezina, vol. 3, pp. 16–19, 1975; and, "Influence of the Type and Concentration of Crosslinking Agent on the Effectiveness of a Combined System of Bismaleimide and Sulfur," Kauchuk i Rezina, No. 10, pp. 15–19, 1985.

However, despite the fact that some of the above patents claim to reduce reversion by addition of a bismaleimide, in actual practice the reduction in reversion achieved with the bismaleimides is insufficient. Accordingly, although the reversion and the heat resistance are slightly improved, the problem remains that there is no generally applicable anti-reversion agent which may be used in combination with a number of different rubber accelerators during the vulcanization process and which satisfactorily solves the reversion problem while at the same time significantly improving the heat resistance of sulfur-vulcanized rubbers without having an adverse affect on other rubber properties.

Further, in Canadian Patent no. 738,500 the vulcanization of rubbers in the absence of sulfur, with either bis-maleimides and biscitraconimides, is disclosed. This process had, for its purpose, to be an alternative to sulfur-vulcanization processes. However, the rubber products made by the process of this patent suffer from the usual disadvantages of peroxide-cured rubbers such as low tensile strength and significant reductions in other important properties. This patent does not disclose the use of the bis-maleimides or biscitraconimides in the sulfur-vulcanization of rubber.

The present invention provides a solution to the above problems by the use of a novel class of (poly)sulfide containing polycitraconimide and polyitaconimide anti-reversion coagents in the sulfur-vulcanization of rubbers.

Compounds of the present invention are represented by the general formula A:

$$(Q_1)_n-D_1-\{(S)_p-D_2-[(S)_q-D_3]_r-(Q_2)_m\}_z (A)$$

wherein $D_1$, $D_2$ and $D_3$, optionally containing one or more heteroatoms or groups selected from nitrogen, oxygen, silicon, phosphorus, boron, sulphone and sulphoxy, is a monomeric or oligomeric divalent, trivalent or tetravelent group and $D_2$ can be nothing when r is not 0; n, m, z are integers independently selected from 1, 2 or 3; p and q are independently selected from integers from 1 to 8; r is an integer selected from 0, 1, 2 and 3; $Q_1$ and $A_2$ are independently selected from the formulas I and II:

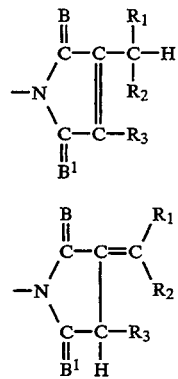

wherein $R_1$, $R_2$ and $R_3$ are independently selected from hydrogen, $C_1$-$C_{18}$ alkyl groups, $C_3$-$C_{18}$ cyctoalkyl groups, $C_6$-$C_{18}$ aryl groups, $C_7$-$C_{30}$ aral kyl groups and $C_7$-$C_{30}$ alkaryl groups and $R_2$ and $R_3$ may combine to form a ring when $R_1$ is hydrogen; B and $B_1$ are independently selected from the following hetero atoms: oxygen and sulfur.

More particularly, in a second aspect, the present invention relates to a sulfur-vulcanized rubber composition which comprises the vulcanization reaction product of:

(A) 100 parts by weight of at least one natural or synthetic rubber;

(B) 0.1 to 25 parts by weight of sulfur and/or a sufficient amount of a sulfur donor to provide the equivalent of 0.1 to 25 parts by weight of sulfur; and (C) 0.1 to 5.0 parts by weight of a coagent of the formula A.

In addition, the present invention relates to a vulcanization process carried out in the presence of the anti-reversion coagents of the formula A and the use of these anti-reversion coagents of the formula A in the sulfur-vulcanization of rubbers. Further, the invention also encompasses rubber products which comprise at least some rubber which has been vulcanized with sulfur in the presence of said anti-reversion coagents of the formula A.

The coagents of the present invention provide an excellent anti-reversion effect as well as improvements in several rubber properties without having a significant adverse effect on the remaining properties, when compared with similar sulfur-vulcanization systems using other coagents.

While not wishing to be bound by any particular theory, it is thought that the anti-reversion coagents of the present invention solve the long-standing problem of reversion in sulfur-vulcanized rubber since they are sufficiently unreactive under sulfur-vulcanization conditions such that, at optimum cure, a substantial portion of the coagent remains in the rubber composition in a form in which it is still capable of reacting with the sulfur-vulcanized rubber to form additional cross-links after optimum cure and during overcure when the problem of reversion occurs. For a definition of optimum cure see, W. Hofmann, "Rubber Technology Handbook."

The compounds of the formula A of the present invention are new compounds and may be prepared by the methods disclosed in, "The synthesis of Biscitraconimides and Polybiscitraconimides," Galanti, A.V. and Scola, D.A., Journ. of Poly. Sci.: Polymer Chemistry Edition, Vol. 19, pp. 451–475, (1981); and "The Synthesis of Bisitaconamic Acids, Isomeric Bisimide Monomers," Galanti, A.V. et al., Journ. Poly. Sci.: Polymer Chemistry Edition, Vol. 20, pp. 233–239 (1982) and Hartford, S.L., Subramanian, S. and Parker, J.A., Journ. Poly. Sci.: Polymer Chemistry Edition, Vol. 16, p. 137, 1982, the disclosures of which are hereby incorporated by reference. Of course, these synthesis methods must be slightly modified by choosing reactants which contain (poly)sulfide groups in order to produce the (poly)sulfide containing imides of the present invention.

The more preferred imide compounds of the present invention and represented by the formula A include, but are not limited to, the biscitraconimides wherein $Q_1$ and $Q_2$ are of the formula I, $R_1=R_2=R_3 H$, n=1 and B=$B_1$=oxygen; the bis-itaconimides wherein $Q_1$ and $Q_2$ are of the formula II, $R_1=R_2=R_3=H$ n=1 and B=$B_1$=oxygen; the mixed citraconimide and itaconimide wherein $Q_1$ is of the formula I, $Q_2$ is of the formula II, $R_1=R_2=R_3=H$, n=1 and B=$B_1$ =oxygen; and mixtures of the above-mentioned compounds.

More specifically, the groups $D_1$, $D_2$ and $D_3$, mentioned in the formula A can be a monomeric divalent, trivalent or tetravalent linear or branched radical chosen from a $C_1$-$C_{18}$ alkyl, $C_2$-$C_{18}$ alkenyl, $C_2$-$C_{18}$ alkynyl, $C_3$-$C_{18}$ cycloalkyl, $C_3$-$C_{18}$ polycycloalkyl, $C_6$-$C_{18}$ aryl, $C_6$-$C_{30}$ polyaryl, $C_7$-$C_{30}$ aralkyl, $C_7$-$C_{30}$ alkaryl, oligomers of one or more of these radicals, and which radicals may optionally contain one or more of oxygen, nitrogen, silicon, phosphorus, sulphone, sulfoxy and boron, all of which radicals may also be optionally substituted at one or more of the atoms in the radical with a substituent selected from oxygen, nitrogen, silicon, $SiO_2$, sulfoxy, boron, phosphorus, amido, imino, azo, diazo, hydrazo, azoxy, alkoxy, hydroxy, iodine, fluorine, bromine, chlorine, carbonyl, carboxy, ester, $SO_2$, $SO_3$ sulphonamido, $SiO_3$, nitro, imido, thiocarbonyl, cyano, and epoxy groups.

More specific examples of some of the imide compounds useful in the present invention include, but are not limited to, the following. bis(2-citraconimidoethyl) sulfide, bis(2-citraconimidoethyl) disulfide, bis(2-citraconimidoethyl) polysulfide, bis(3-citraconimidopropyl) disulfide, bis(4-citraconimido-2-methylbutyl) disulfide, bis(2-citraconimidocyclohexyl) disulfide, 2-citraconimidoethyl -3-citraconimidopropyl sulfide, 1,2-bis( 2-citraconimidophenylthio)-ethane, 1,2-bis(2-citraconimido-5-chlorophenylthio)-ethane, 1,4-bis(2-citraconimidophenylthio)-butene-2, 1,3-bis(2-citraconimidophenylthio)-propanone-2, $\alpha,\alpha'$-bis( 2-citraconimidophenylthio)-m-xylene, 2-citraconimidoethyl-2-citraconimidophenyl sulfide, bis(4-citraconimidophenyl) disulfide, bis(4-citraconimido-3-chlorophenyl) disulfide, bis(2-citraconimidophenyl) disulfide, bis(2-citraconimidophenyl) sulfide, bis(2-citraconimidophenyl) tetrasulfide, bis(2-citraconimido-4-methoxyphenyl)disulfide, 2,4,6-tris(2-citraconimidoethylthio) -1,3,5-cyanurate, 2,5-bis (2-citraconimidoethylthio)-1,3,4-thiadiazole, bis(4-citraconimido-2,6-dimethylphenyl) disulfide, bis(2'- citraconimidoethoxyethyl) disulfide and bis(3,5 -dicitraconimidophenyl) disulfide.

In addition, the bis-, tris- and tetra-itaconimides of the present invention may be the same as mentioned above, except that all citraconimide groups are exchanged for itaconimide groups. The same materials as mentioned above may also be mixed imides if some of the citraconimide groups are exchanged for itaconimide groups.

The compounds of the present invention may be used in the vulcanization of all natural and synthetic rubbers. Examples of such rubbers include, but are not limited to, natural rubber, styrene-butadiene rubber, butadiene rubber, isoprene rubber, acrylonitrile-butadiene rubber, chloroprene rubber, isoprene-isobutylene rubber, brominated isoprene-isobutylene rubber, chlorinated isoprene-isobutylene rubber, ethylene-propylene-diene terpolymers, as well as combinations of two or more of these,rubbers and combinations of one or more of these rubbers with other rubbers and/or thermoplastics.

Examples of sulfur which may be used in the present invention include various types of sulfur such as powdered sulfur, precipitated sulfur and insoluble sulfur. Also, sulfur donors may be used in place of, or in addition to sulfur in order to provide the required level of sulfur during the vulcanization process. Examples of such sulfur donors include, but are not limited to, tetramethylthiuram disulfide, tetraethylthiuram disulfide, tetrabutylthiuram disulfide, dipentamethylene thiuram hexasulfide, dipentamethylene thiuram tetrasulfide, dithiodimorpholine and mixtures thereof.

In this text, references to sulfur shall include sulfur donors and mixtures of sulfur and sulfur donors. Further, references to the quantity of sulfur employed in the vulcanization, when applied to sulfur donors, refer to a quantity of sulfur donor which is required to provide the equivalent amount of sulfur that is specified.

The amount of sulfur to be compounded with the rubber is, based on 100 parts of rubber, usually 0.1 to 25 parts by weight, and more preferably 0.2 to 8 parts by weight. The amount of sulfur donor to be compounded with the rubber is an amount sufficient to provide an equivalent amount of sulfur which is the same as if sulfur itself were used.

The amount of anti-reversion coagent of the formula A to be compounded with the rubber is, based on 100 parts of rubber, 0.1 to 5 parts by weight, and more preferably 0.2 to 3.0 parts by weight. These ingredients may be employed as a pre-mix, or added simultaneously or separately, and they may be added together with other rubber compounding ingredients as well.

In most circumstances it is also desirable to have a vulcanization accelerator in the rubber compound. Conventional, known vulcanization accelerators may be employed. The preferred vulcanization accelerators include mercaptobenzothiazole, 2,2'-mercaptobenzothiazole disulfide; sulfenamide accelerators including N-cyclohexyl-2-benzothiazole sulfenamide, N-tertiary-butyl-2-benzothiazole sulfenamide, N,N'-dicyclohexyl-2-benzothiazole sulfenamide, and 2-(morpholinothio)-benzothiazole; thiophosphoric acid derivative accelerators, thiurams, dithiocarbamates, diphenyl guanidine, diorthotolyl guanidine, dithiocarbamylsulfenamides, xanthates, triazine accelerators and mixtures thereof.

The vulcanization accelerator is employed in quantities of from 0.1 to 8 parts by weight, based on 100 parts by weight of rubber composition. More preferably, the vulcanization accelerator comprises 0.3 to 4.0 parts by weight, based on 100 parts by weight of rubber.

Other conventional rubber additives may also be employed in their usual amounts. For example, reinforcing agents such as carbon black, silica, clay, whiting and other mineral fillers, as well as mixtures of fillers, may be included in the rubber composition. Other additives such as process oils, tackifiers, waxes, antioxidants, antiozonants, pigments, resins, plasticizers, process aids, factice, compounding agents and activators such as stearic acid and zinc oxide may be included in conventional, known amounts. For a more complete listing of rubber additives which may be used in combination with the present invention see, W. Holmann, "Rubber Technology Handbook", Chapter 4, Rubber Chemicals and Additives, pp. 217–353, Hanser Publishers, Munich 1989.

Further, scorch retarders such as phthalic anhydride, pyromellitic anhydride, benzene hexacarboxylic trianhydride, 4-methylphthalic anhydride, trimellitic anhydride, 4-chlorophthalic anhydride, N-cyclohexyl-thiophthalimide, salicylic acid, benzoic acid, maleic anhydride and N-nitrosodiphenylamine may also be included in the rubber composition in conventional, known amounts. Finally, in specific applications it may also be desirable to include steel-cord adhesion .promoters such as cobalt salts and dithiosulfates in conventional, known quantities.

The present invention also relates to a vulcanization process which comprises the step of vulcanizing at least one natural or synthetic rubber in the presence of 0.1 to 25 parts by weight of sulfur or a sulfur donor per 100 parts by weight of rubber, characterized in that said process is carried out in the presence of an effective amount of a coagent of the formula A.

The process is carried out at a temperature of 110°–220° C. over a period of up to 24 hours. More preferably, the process is carried out at a temperature of 120°–190° C. over a period of up to 8 hours in the presence of 0.1 to 5.0 parts by weight of anti-reversion coagent. Even more preferable is the use of 0.2–3.0 parts by weight of anti-reversion coagent. All of the additives mentioned above width respect to the rubber composition may also be present during the vulcanization process of the invention.

In a more preferred embodiment of the vulcanization process, the vulcanization is carried out at a temperature of 120°–190° C. over a period of up to 8 hours and in the presence of 0.1 to 8.0 parts by weight, based on 100 parts by weight of rubber, of at least one vulcanization accelerator.

The present invention also comprises the use of an anti-reversion coagent of the formula A in a process for the sulfur-vulcanization of rubber.

Finally, the present invention also includes articles of manufacture, such as tires, which comprise sulfur-vulcanized rubber which is vulcanized in the presence of the anti-reversion coagents of the formula A.

The invention is further illustrated by the following examples which are not to be construed as limiting the invention in any way. The scope of the invention is to be determined from the claims appended hereto. The 1H-NMR spectra were recorded on a Bruker WP 200 SY using TMS as internal standard.

Example 1

Synthesis of bis(2-citraconimidoethyl) disulfide. To a stirred slurry of 28.15 g. of cystamine.2HCL and 22g. sodium acetate in 150 ml. of xylene, was added 28.10 g. of citraconic anhydride. The mixture was then heated to reflux and the formed water was trapped in a Dean-Stark apparatus. After the formation of water stopped the slurry was cooled and the salts were removed by filtration. The clear solution was distilled in vacuo to remove xylene. The resulting viscous dark colored oil (41.5 g.) slowly crystallized upon standing. After recrystallization from ethanol, a cream colored product was obtained having a melting point of 74.3°–75.2° C. 1H-NMR identified the product as bis(2-citraconimidoethyl) disulfide.

Example 2

Synthesis of bis(4-citraconimidophenyl) disulfide. To a stirred slurry of 31 g. of p,p'-diaminodiphenyldisulfide in 150 ml. xylene, was added 28.10 g. of citraconic anhydride. The mixture was heated to reflux and the formed water was trapped in a Dean-Stark apparatus. After the formation of water stopped the slurry was cooled and the product was removed by filtration and washed twice with xylene. The product (48.6 g.) was dried in vacuo. 1H-NMR identified the product as bis(4-citraconimidophenyl) disulfide.

Example 3

Synthesis of 1,2-bis(2-citraconimidophenylthio)-ethane. To a stirred solution of 100 g. of 1,2-bis(2-aminophenylthio)-ethane, which was prepared according to the procedure described in U.S. Pat. No. 3,920,617, in 350 ml. xylene, was added 81.16 g. of citraconic anhydride. The mixture was heated to reflux and the formed water was trapped in a Dean-Stark apparatus. After the formation of water stopped, the solution was cooled and distilled in vacuo to remove xylene. The resulting viscous dark oil (163 g.) slowly solidifies upon standing. 1H-NMR identified the product as 1,2-bis(2-citraconimidophenylthio)-ethane.

Example 4

Synthesis of 2-Citraconimidophenyl-2-citraconimidoethyl sulfide. To a stirred solution of 50 g. of 2-(2-aminophenylthio)-ethaneamine, which was prepared according to the procedure described in German patent publication DE 27 34 574, in 250 ml. of xylene, was added 67.2 g. of citraconic anhydride. The mixture was heated to reflux and the formed water was trapped in a Dean-Stark apparatus. After the formation of water stopped, the solution was cooled and distilled in vacuo to remove xylene. The resulting viscous dark colored oil (103.5 g.) slowly solidified upon standing. 1H-NMR identified the product as 2-citraconimidophenyl-2-citraconimidoethyl sulfide.

Example 5

Synthesis of 1,4-bis(2-citraconimidophenylthio)-butene-2. To a stirred solution of 125 g. of 1,4-bis(2-aminophenylthio)-2-butene, which was prepared in accordance with the procedure described in U.S. Pat. No. 3,920,617, in 350 ml. of xylene, was added 92.74 g. of citraconic anhydride. The mixture was heated to reflux and the formed water was trapped in a Dean-Stark apparatus. After the formation of water stopped, the solution was cooled and distilled in vacuo to remove xylene. The resulting viscous dark colored oil (193 g.) slowly solidifies upon standing. 1H-NMR identified the product as 1,4-bis(2-citraconimidophenylthio)-butene-2.

Example 6

Synthesis of bis-(2-citraconimidophenyl)-disulfide. To a stirred slurry of 100 g. of partially dissolved 2-aminophenyl disulfide in 350 ml. xylene was added 90.9 g. citraconic anhydride. The mixture was heated to reflux and the formed water was trapped in a Dean-Stark apparatus. After the formation of water stopped, the solution was cooled to room temperature. The solids were removed by filtration and washed twice with 100 ml. of xylene and dried in vacuo to yield 59.9 g. of a cream-colored product having a melting point of 185.5°–187° C. The xylene fractions were combined and the xylene was removed in vacuo. The resulting black oil was refluxed in 300 ml. of ethanol. The ethanol solution was cooled to 5° C. and the solids were removed by filtration and dried in vacuo to yield an extra 14.4 g. of product melting at 185.5°–186.8° C. 1H-NMR confirmed that both products were bis-(2-citraconimidophenyl) disulfide.

Examples 714 11 and Comparative Example A

Natural Rubber Compound: torque retention in Monsanto rheograms of a natural rubber compound vulcanized with five different coagents of the formula A.

| Base compound (Compound A = control) | |
| --- | --- |
| NR: SMR CV5 | 100 parts |
| Carbon black N330 | 50 phr |
| Stearic acid | 2 phr |
| Zinc Oxide RS | 5 phr |
| Dutrex 729 HP ® | 3 phr |
| CBS | 0.6 phr |
| sulfur | 2.3 phr. |

(Poly)sulfide-containing polycitraconimides tested:

1. bis(2-citraconimidophenyl) disulfide (BCI-oPh2)
2. bis(4-citraconimidophenylthio) ethane (BCI-PTE)
3. bis(2-citraconimidophenylthio) ethane (BCI-OPTE)
4. bis(2-citraconimidoethyl) disulfide (BCI-ES2)
5. bis(4-citraconimidophenyl) disulfide (BCI-Ph2)

Compounding: Banbury 1.6 liter, 70% load factor, 77 rpm, start temp. 50° C., mixing time 6 min; Two-roll mill (vulcanisation agents and BCI): roller friction 1:1.22, start temp. 40°–50° C., 3 min. Vulcanization curve: Monsanto Rheometer MDR 2000E, arc 0.5°, temp. 170° C. and 180° C., up to 60 min. % Torque retention is the final torque divided by the maximum torque of the vulcanization curve (Table 1).

TABLE 1

| Cmp # | BCI — | Conc. phr | Temp. °C. | time min | % Torque retention | control (A) |
|---|---|---|---|---|---|---|
| 7 | oPh2 | 1.0 | 170 | 30 | 86 | 74 |
| 8 | PTE | 1.1 | 170 | 60 | 87 | 71 |
| 9 | OPTE | 1.4 | 170 | 60 | 81 | 70 |
| 10 | ES2 | 1.7 | 180 | 60 | 123 | 66 |
| 11 | Ph2 | 2.2 | 180 | 60 | 119 | 66 |

(Poly)sulfide-containing polycitraconimides showed improved torque retention after overcure at relatively high temperatures as compared to the control, indicating improved reversion resistance of the compounds with (poly)sulfide-containing polycitraconimides.

Examples 12–13 and Comparative Example B

Natural Rubber Compound: vulcanization characteristics and properties. Sheets were vulcanized by compression moulding at 150° and 180° C. to optimum cure ($t_{90}$) and overcured for 30 min and 60 rain, respectively.

| Test methods | |
|---|---|
| Tensile Strength | ISO 37/2 - Dumb bell |
| Elongation at Break | ISO 37/2 - Dumb bell |
| Modulus | ISO 37/2 - Dumb bell |
| Hardness | ISO 48 (IRHD) or DIN 53505 (Shore A) |
| Elasticity | ISO 4662 |
| Compression Set | ISO R 815; 72 hours at 23° C. |

Mechanical properties of the compounds made in Examples 10 and 11, respectively, have been determined, and compared with the control (Example B) (Tables 2 and 3).

TABLE 2

Physical and Mecnanical Properties of Compounds Vulcanized at 150° C. to optimum cure (after 30 min.).

| Test | B (No BCI) | 12 (BCI-ES2) | 13 (BCI-Ph2) |
|---|---|---|---|
| Hardness (IRHD) | 70 | 70 | 75 |
| Tensile Strength (MPa) | 27.8 | 27.2 | 27.4 |
| Elongation (%) | 490 | 500 | 490 |
| Modulus 50% (MPa) | 1.6 | 1.6 | 1.9 |
| Modulus 100% (MPa) | 3.2 | 3.2 | 3.7 |
| Modulus 300% (MPa) | 16.1 | 15.7 | 16.3 |
| Rebound Resilience (%) | 36 | 36 | 35 |
| Compression Set (%) | 11 | 11 | 15 |

TABLE 3

Physical and Mechanical Properties of Compounds Vulcanized 1 hour at 180° C.

| Test | B (No BCI) | 12 (BCI-ES2) | 13 (BCI-Ph2) |
|---|---|---|---|
| Hardness (IRHD) | 60 | 72 | 78 |
| Tensile Strength (MPa) | 17.0 | 22.5 | 17.9 |
| Modulus 50% (MPa) | 1.1 | 1.9 | 2.6 |
| Modulus 100% (MPa) | 1.8 | 3.9 | 5.2 |
| Modulus 300% (MPa) | 9.2 | 20.2 | — |
| Rebound Resilience (%) | 31 | 35 | 32 |
| Compression Set (%) | 20 | 12 | 19 |

BCI-ES2 and BCI-Ph2-containing compounds showed substantially improved mechanical properties after overcure at relatively high temperature (180° C.) as compared to the control: higher hardness, tensile strength, modulus and resilience, and lower compression set.

Example 14 and Comparative Example C

Truck tire tread compound A truck tire compound consisting of a NR/BR blend cured with a semi-E.V. cure system (recipe derived from C.S.L. Baker et al., Elastomerics, Jul. 1989, pp. 20, see Recipe) was prepared with BCI-ES2.

| Recipe Ingredient | 14 | C |
|---|---|---|
| NR SMR 20 | 80.00 | 80.00 |
| BR Buna CB 10 | 20.00 | 20.00 |
| Carbon Black N-375 | 55.00 | 55.00 |
| Stearic Acid | 2.00 | 2.00 |
| Zinc Oxide RS | 4.00 | 4.00 |
| Aromatic Oil Dutrex 729 HP ® | 8.00 | 8.00 |
| Permanex 6PPD ® | 2.00 | 2.00 |
| BCI-ES2 | 1.00 | — |
| Perkacit CBS c ® | 1.20 | 1.20 |
| Sulfur | 1.20 | 1.20 |

Compounding: Banbury 5.0 liter, 70% load factor, 40 rpm, start temp. 50° C., mixing time 6 min; Two-roll mill (vulcanization agents and BCI): roller friction 1:1.22, start temp. 40°–50° C., 3 min. Sheets were vulcanized by compression moulding at 150° and 170° C. to optimum cure ($t_{90}$) and overcured for 60 min and 30 min, respectively.

| Test methods in addition to those previously set forth above | |
|---|---|
| Mooney Viscosity | ISO R-289 - ML 100° C. |
| Mooney Scorch | ISO R-289 - ML 121° C. |
| Rheology | Monsanto MDR 2000E |
| Elasticity | ISO 4662 |
| Tear Resistance | ISO 34 - Crescent With 1 mm cut |
| Abrasion | DIN 53.516 |
| Hot Air Ageing | ISO 188 - 1 & 3 days at 100° C. |
| Compression Set | ISO R 815; 1 day at 23° C. |
| Fatigue to Failure | ASTM D4482/cam 24/8 samples |
| Goodrich Flexometer | ASTM D623A/T initial 100° C./30 Hz |

In addition, the rheology was measured at several different times and temperatures using a range of 2.5 Nm and an arc of 0.5°. BCI-ES2 has practically no effects on Mooney viscosity and scorch time (Table 4). Table 5 gives the cure characteristics at different temperatures.

TABLE 4

| Property | Control (C) | BCI-ES2 (14) |
|---|---|---|
| Mooney viscosity | 46.4 | 44.9 |
| Scorch time (min) | 36.1 | 35.1 |

TABLE 5

| Monsanto rheometer cure data | Control (C) | BCI-ES2 (14) |
|---|---|---|
| Temperature: 140° C. | | |
| $t_s2$ (min) | 10.1 | 10.7 |
| delta torque (Nm) | 1.53 | 1.45 |
| Temperature: 180° C. | | |
| $t_s2$ (min) | 0.83 | 0.95 |
| delta torque (Nm) | 1.33 | 1.23 |

Table 6 gives the torque retention in the cure curve determined in the Monsanto rheometer at 140° C. during a prolonged curing time of up to 8 hours. BCI-ES2 had a substantial (over)compensating effect on the reversion in the rubber.

TABLE 6

| | Torque retention (%) |
|---|---|
| control (C) | 77 |
| BCI-ES2 (14) | 121 |

Table 7 shows the improvement of various properties of the vulcanizates after overcure at 150° and 170° C.: improved hardness, rebound resilience, tensile strength, modulus, abrasion, tear strength, heat build up and permanent set. Elongation, compression set and fatigue were not substantially changed. The values given are at optimum cure and the values in parentheses are at 60 minutes cure for 150° C. and at 30 minutes cure for 170° C.

TABLE 7

| | 150° C. | | 170° C. | |
|---|---|---|---|---|
| Test | C (No BCI) | 14 (BCI-ES2) | C (No BCI) | 14 (BCI-ES2) |
| Hardness (IRHD) | 70 | 70 | 69 | 68 |
| | (67) | (72) | (63) | (70) |
| Tensile Strength (MPa) | 25.5 | 25.0 | 25.1 | 24.5 |
| | (21.9) | (23.1) | (16.8) | (22.3) |
| Elongation (%) | 540 | 550 | 580 | 600 |
| | (540) | (460) | (530) | (500) |
| Modulus 50% (MPa) | 1.2 | 1.2 | 1.2 | 1.1 |
| | (1.1) | (1.4) | (1.0) | (1.3) |
| Modulus 100% (MPa) | 2.4 | 2.1 | 2.1 | 1.9 |
| | (1.9) | (2.6) | (1.5) | (2.2) |
| Modulus 300% (MPa) | 12.5 | 11.9 | 11.2 | 10.0 |
| | (10.5) | (13.7) | (7.6) | (11.4) |
| Abrasion (mm³) | 93 | 90 | 83 | 96 |
| | (128) | (79) | (126) | (80) |
| Compression Set (%) 72 hours, 23° C. | 10.2 | 12.2 | 11.0 | 12.9 |
| | (14.5) | (13.1) | (17.5) | (12.2) |
| Tear Strength (kN/m) | 115 | 103 | 105 | 109 |
| | (88) | (100) | (43) | (72) |
| Permanent Set (%) | 13.1 | 10.1 | 14.0 | 13.4 |
| | (13.9) | (5.4) | (17.9) | (6.6) |
| Heat Build Up (°C.) | +40 | +27 | +39 | +29 |
| | (+47) | (+25) | (+58) | (+27) |

Improved properties of the compound containing BCI-ES2 in comparison with the control were also observed after ageing (Tables 8 & 9).

TABLE 8

Ageing of the 150° C., optimum cure cured rubbers for 24 and 72 hours and in parentheses are the values obtained by ageing the 150° C., 60 minute cured rubbers for 24 and 72 hours. All ageing was carried out at 100° C.

| | 24 Hours | | 72 Hours | |
|---|---|---|---|---|
| Test | C (No BCI) | 14 (BCI-ES2) | C (No BCI) | 14 (BCI-ES2) |
| Hardness (IRHD) | 74 | 74 | 73 | 74 |
| | (70) | (72) | (68) | (74) |
| Tensile Strength (MPa) | 26.0 | 25.8 | 21.4 | 22.8 |
| | (20.1) | (24.6) | (16.7) | (19.8) |
| Modulus 50% (MPa) | 1.8 | 1.7 | 1.9 | 2.0 |
| | (1.4) | (1.8) | (1.5) | (2.1) |
| Modulus 100% (MPa) | 3.5 | 3.5 | 3.7 | 3.9 |
| | (2.5) | (3.6) | (2.8) | (4.2) |
| Modulus 300% (MPa) | 16.4 | 16.0 | 16.0 | 16.8 |
| | (12.0) | (16.9) | (12.5) | (17.6) |

TABLE 9

Ageing of the 170° C., optimum cure cured rubbers for 24 and 72 hours and in parentheses are the values obtained by ageing the 170° C., 30 minute cured rubbers for 24 and 72 hours. All ageing was carried out at 100° C.

| | 24 Hours | | 72 Hours | |
|---|---|---|---|---|
| Test | C (No BCI) | 14 (BCI-ES2) | C (No BCI) | 14 (BCI-ES2) |
| Hardness (IRHD) | 73 | 73 | 74 | 75 |
| | (65) | (72) | (67) | (73) |
| Tensile Strength (MPa) | 25.3 | 25.5 | 20.2 | 20.1 |
| | (15.6) | (21.1) | (12.9) | (17.1) |
| Modulus 50% (MPa) | 1.7 | 1.7 | 1.8 | 1.9 |
| | (1.2) | (1.6) | (1.4) | (1.9) |
| Modulus 100% (MPa) | 3.4 | 3.3 | 3.5 | 3.7 |
| | (1.9) | (2.9) | (2.3) | (3.5) |
| Modulus 300% (MPa) | 15.8 | 15.5 | 15.5 | 16.2 |
| | (9.0) | (14.2) | (9.8) | (15.3) |

Example 15 and Comparative Example D

Steel-cord reinforced NR compound A steel-cord skim stock (see TABLE 10) was compounded with BCI-ES2 following procedure as in Example 7. The compounds were vulcanized by compression moulding at 150° and 170° C. up to optimum cure and overcured at 170° C. for 30 min.

TABLE 10

| Ingredient | 15 | D |
|---|---|---|
| NR SMR CV | 100.00 | 100.00 |
| Carbon Black N-326 | 55.00 | 55.00 |
| Stearic Acid | 0.50 | 0.50 |
| Zinc Oxide | 8.00 | 8.00 |
| Aromatic Oil Dutrex 729 HP ® | 3.00 | 3.00 |
| Permanex 6PPD ® | 2.00 | 2.00 |
| BCI-ES2 | 1.00 | — |
| Perkacit CBS ® | 0.70 | 0.70 |
| Crystex OT 20 ® | 5.00 | 5.00 |

The following test methods in addition to those mentioned above, were used.
Steel Cord Adhesion : ASTM D-2295
Steam Ageing : 8 hrs. at 119 ° C. and 1 bar TABLE 11 shows that BCI-ES2 had no effect on scorch and that delta torque was increased.

TABLE 11

| | D Control | 15 BCI-ES2 |
|---|---|---|
| Temperature 150° C. | | |
| Monsanto rheometer cure data | | |
| Scorch MS 121° C. | 21.0 | 21.2 |
| t$_s$2 (min) | 2.9 | 3.0 |
| delta torque (Nm) | 1.9 | 2.3 |
| Temperature: 170° C. | | |
| Monsanto rheometer cure data | | |
| t$_s$2 (min) | 0.7 | 0.8 |
| delta torque (Nm) | 1.8 | 2.1 |

TABLE 12 shows that BCI-ES2 maintained or improved various mechanical properties such as hardness, tensile strength, modulus and tear strength, especially after overcure at 170° C. BCI-ES2 also improved the steel-cord adhesion.

TABLE 12

| | 150° C. | | 170° C. | |
|---|---|---|---|---|
| Optimum Cure at Test | D (No BCI) | 15 (BCI-ES2) | D (No BCI) | 15 (BCI-ES2) |
| Hardness (IRHD) | 66 | 71 | 64 | 68 |
| Tensile Strength (MPa) | 25.8 | 25.4 | 25.5 | 25.9 |
| Modulus 50% (MPa) | 1.5 | 2.3 | 1.5 | 1.7 |
| Modulus 100% (MPa) | 2.7 | 3.8 | 2.7 | 3.2 |
| Modulus 300% (MPa) | 12.4 | 15.5 | 11.6 | 13.6 |
| Tear Strength (kN/m) | 114 | 98 | 107 | 102 |
| Steelcord Adhesion (N) | 290 | 350 | 180 | 190 |

| Cure for 30 minutes at | 170° C. | |
|---|---|---|
| Test | D (No BCI) | 15 (BCI-ES2) |
| Hardness (IRHD) | 55 | 65 |
| Tensile Strength (MPa) | 19.0 | 22.2 |
| Modulus 50% (MPa) | 1.2 | 1.8 |
| Modulus 100% (MPa) | 1.8 | 3.1 |
| Modulus 300% (MPa) | 7.9 | 13.6 |
| Tear Strength (kN/m) | 35 | 50 |
| Steelcord Adhesion (N) | 410 | 440 |

Example 16, Comparative Example E (Bismaleimide compound) and Comparative Example F (control without coagent). NR compound with BCI-Ph2 (comparison with bis(4-maleimidophenyl) disulfide (BMI-Ph2) and the control (Example F))

A NR base compound (NR SMR CV5 100 parts, carbon black N-330 50 phr, Stearic acid 2 phr, ZnO 5 phr, Perkacit ® MBTS 1.0 phr, sulfur 2.25 phr) was mixed with 3.3 phr BCI-Ph2 and 3.0 phr BMI-Ph2 (7.5 mmole/100 g of each material). The compound containing BCI-Ph2 showed no reversion and a higher torque retention in the cure curve at 180° C. after 50 min than the control and the compound with BMI-Ph2, which both showed significant reversion (TABLE 13):

TABLE 13

| | Torque retention (%) |
|---|---|
| control (F) | 67 |
| BCI-Ph2 (16) | 121 |
| BMI-Ph2 (E) | 79 |

After vulcanisation at 180° C. to optimum cure and overcure (60 min) the compound containing BCI-Ph2 showed improved mechanical properties over the control, especially after overcure (TABLE 14):

TABLE 14

| compound | control | | BCI-Ph2 | |
|---|---|---|---|---|
| Cure time | t$_{90}$ | 60 min | t$_{90}$ | 60 min |
| hardness (Sh A) | 15 | 13 | 17 | 23 |
| tensile strength (MPa) | 18.6 | 13.4 | 21.6 | 17.0 |
| Modulus (MPa) | | | | |
| 100% | 1.5 | 1.5 | 2.0 | 4.1 |
| 300% | 7.2 | 6.2 | 9.4 | 16.0 |

What is claimed is:

1. A compound of the general formula A:

$$(W_1)_n - D_1 - \{(S)_p - D_2 - [(S)_q - D_3]_r - (Q_2)_m\}_z \text{ (A)};$$

wherein $D_1$, $D_2$ and $D_3$ are independently selected from the following group of monomeric or oligomeric divalent, trivalent or tetravalent, linear or branched radicals: $C_1C_{18}$ alkyl, $C_2$-$C_{18}$ alkenyl, $C_2$-$C_{18}$ alkynyl, $C_3$-$C_{18}$ cycloalkyl, $C_3$-$C_{18}$ polycycloalkyl, $C_6$-$C_{18}$ aryl, $C_6$-$C_{30}$ polyaryl, $C_7$-$C_{30}$ aralkyl, $C_7$-$C_{30}$ alkaryl, all of which radicals may be optionally substituted with one or more hetero atoms selected from oxygen, nitrogen, silicon, phosphorus, and/or with one or more functional groups selected from sulphone, sulphoxy, boron, $SiO_2$, amido, imino, azo, diazo, hydrazo, azoxy, alkoxy, halogen, carbonyl, carboxy, ether, $SO_2$, $SO_3$ sulphonamido, $SiO_3$, nitro, imido, thiocarbonyl, cyano, and epoxy, and wherein $D_2$ can be nothing when r is not 0; n, m, z are integers independently selected from 1, 2 or 3; p and q are independently selected from integers from 1 to 8; r is an integer selected from 0, 1, 2 and 3; $Q_1$ and $Q_2$ are independently selected from the formulas I and II:

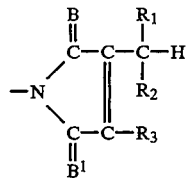

(I)

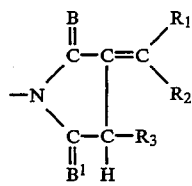

(II)

wherein $R_1$, $R_2$ and $R_3$ are independently selected from hydrogen, $C_1$-$C_{18}$ alkyl groups, $C_3$-$C_{18}$ cycloalkyl groups, $C_6$-$C_{18}$ aryl groups, $C_7$-$C_{30}$ aralkyl groups and $C_7$-$C_{30}$ alkaryl groups and $R_2$ and $R_3$ may combine to form a ring when $R_1$ is hydrogen; B and $B^1$ are independently selected from the following hetero atoms: oxygen and sulfur.

2. The compound of claim 1 wherein $R_1$, $R_2$ and $R_3$ are hydrogen and B and $B_1$ are oxygen.

3. The compound of claim 2 wherein $D_1$, $D_2$ and $D_3$ are independently selected from divalent ethyl and divalent phenyl radicals, and when r is not 0, $D_2$ may be nothing.

4. The compound of claim 3 wherein r is not 0, and $D_2$ is nothing.

5. The compound of claim 1 wherein r is 0.

6. The compound of claim 1 wherein p and q are 1.

7. A sulfur-vulcanized rubber composition which comprises the vulcanization reaction product of:
(A) 100 parts by weight of at least one natural or synthetic rubber;
(B) 0.1 to 25 parts by weight of sulfur and/or a sufficient amount of a sulfur donor to provide the equivalent of 0.1 to 25 parts by weight of sulfur; and
(C) 0.1 to 5.0 parts by weight of a compound as claimed in claim 1.

8. A sulfur-vulcanized rubber composition as claimed in claim 7 wherein said rubber composition further comprises 0.1 to 8.0 parts by weight of a vulcanization accelerator.

9. A sulfur-vulcanized rubber composition as claimed in claim 7 which comprises 0.1 to 5.0 parts by weight of unreacted compound of the formula A after optimum cure.

10. A process for the vulcanization, at a temperature of from 110° to 220° C. for up to 24 hours, of a vulcanizable composition comprising at least one natural or synthetic rubber in the presence of 0.1 to 25 parts by weight of sulfur or a sufficient amount of a sulfur donor to provide the equivalent of 0.1 to 25 parts by weight of sulfur, characterized in that said process is carried out in the presence of an effective amount of a compound as claimed in claim 1.

11. A vulcanization process as claimed in claim 10, wherein said rubber is vulcanized in the further presence of 0.1 to 8.0 parts by weight of a vulcanization accelerator.

12. A process for the sulfur-vulcanization of rubber which comprises employing as an anti-reversion agent an effective amount of a compound as claimed in claim 1.

13. An article of manufacture comprising a rubber vulcanized by the process of claim 10.

14. A tire comprising a rubber vulcanized by the process of claim 10.

* * * * *

UNITED STATES PATENT AND TRADEMARK OFFICE
CERTIFICATE OF CORRECTION

PATENT NO. : 5,405,918

DATED : April 11, 1995

INVENTOR(S) : Hogt, Andreas H. et al.

It is certified that error appears in the above-indentified patent and that said Letters Patent is hereby corrected as shown below:

Column 14:

In claim 1, line 2, the letter "$(W_1)_n$" should be --$(Q_1)_n$--; and line 6, "$C_1C_{18}$" should read --$C_1-C_{18}$--;

Signed and Sealed this

Fifteenth Day of August, 1995

Attest:

BRUCE LEHMAN

*Attesting Officer*  *Commissioner of Patents and Trademarks*